US006660132B1

(12) United States Patent
Demuth et al.

(10) Patent No.: US 6,660,132 B1
(45) Date of Patent: Dec. 9, 2003

(54) PHOTOCHEMICAL AND THERMOCHEMICAL SOLAR SYNTHESES USING FLAT-BED SOLAR COLLECTORS/ SOLAR REACTORS

(75) Inventors: Martin Demuth, Mülheim an der Ruhr (DE); Alfred Ritter, Mülheim an der Ruhr (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/673,268

(22) PCT Filed: Apr. 17, 1999

(86) PCT No.: PCT/EP99/02597

§ 371 (c)(1), (2), (4) Date: Oct. 13, 2000

(87) PCT Pub. No.: WO99/54032

PCT Pub. Date: Oct. 28, 1999

(30) Foreign Application Priority Data

Apr. 17, 1998 (DE) ........................................ 198 16 876
Sep. 25, 1998 (DE) ........................................ 198 44 037

(51) Int. Cl.[7] .......................... C07F 5/00; C07C 401/00
(52) U.S. Cl. ............................... 204/157.6; 204/157.4; 204/157.67
(58) Field of Search ......................... 204/157.6, 157.67, 204/157.4

(56) References Cited

U.S. PATENT DOCUMENTS 4,004,573 A * 1/1977 Frieling et al. ............. 126/271
4,478,699 A * 10/1984 Halmann et al. ....... 204/158 R
4,609,444 A * 9/1986 Guillet .................... 204/157.6
5,543,016 A * 8/1996 Fehlner et al. ........... 204/157.6

FOREIGN PATENT DOCUMENTS

| | | | |
|---|---|---|---|
| DE | 2712411 A | * | 10/1978 |
| DE | 3727630 C1 | * | 10/1988 |
| DE | 4344163 A | * | 6/1995 |
| EP | 761808 A2 | * | 3/1997 |
| JP | 59-4436 A | * | 1/1984 |
| JP | 2-40453 A | * | 2/1990 |

OTHER PUBLICATIONS

*References A–C and N–S were cited in the International Search Report.*

* cited by examiner

*Primary Examiner*—Edna Wong
(74) *Attorney, Agent, or Firm*—Norris McLaughlin & Marcus

(57) ABSTRACT

The invention relates to a method for carrying out photochemical and thermochemical solar syntheses by means of flat-bed solar light collectors without devices for focusing the sunlight. The method is particularly well suited for producing flavors, aromas and complex thereof. The flat-bed solar light collector is suitable especially for producing steroids and derivatives thereof. It can further be used for the photooxidation (photooxygenation) of terpene olefins and therefore for the synthesis of fragrants such as rose oxide, myrtenol and myrtenal which are of industrial interest. The solar collector is also suitable for photochemical addition reactions and rearrangements.

14 Claims, 1 Drawing Sheet

① Glass or plastic film (with valve)
② Reaction chamber
③ Reaction chamber floor(can be mirrored and/or surface-structured)
④ Cooling chamber (e.g. water cooling)
⑤ Heat exchanger
⑥ Ground ① Glass or plastic film (with valve)
② Reaction chamber
③ Reaction chamber floor(can be mirrored and/or surface-structured)
④ Cooling chamber (e.g. water cooling)
⑤ Heat exchanger
⑥ Ground

PHOTOCHEMICAL AND THERMOCHEMICAL SOLAR SYNTHESES USING FLAT-BED SOLAR COLLECTORS/ SOLAR REACTORS

This application is a 371 of PCT/EP99/02597, which was filed on Apr. 17, 1999.

The invention relates to a method for carrying out photochemical and thermochemical solar syntheses by means of flat-bed solar light collectors without devices for focusing or concentrating the sunlight and does not need sun tracking.

Several solar technical devices have been disclosed in DE 4134614 C2 for the conduction of solar photochemical reactions wherein the solar radiation does not reach the reaction medium directly, but only upon passing an auxiliary device for the concentration of the light. Since the emitted solar radiation is, dependent on geografical situation and weather, differently dispersed as diffuse radiation and is hence only partially available for concentration purpose. Therefore, light concentrating solar devices leave a considerable portion of the solar radiation for photochemical reactions unused. It is emphasized in DE 43 44163 Al that less by-products are obtained at higher conversions in the photooxidation of terpene olefins if working with high concentration of radiation.

Otherwise, the application of concentrating or focussing devices is at our geographical latitudes, lacking direct solar radiation, disadvantageous for (photo)chemical transformations.

Surprisingly, it has now been found that this aggravating disadvantage using solar radiation energy for photo- and thermochemical purpose can be avoided by employing a technically simpler and hence cheaper flat-bed solar light collector since it is suited to use diffuse solar radiation as well as artificial light without significant changes of product ratios in the reactions carried out under these conditions. Furthermore, the combination of solar and arificial (for night runs) light allows continuous production. Further, it was found that the claim by Scharf (Angew. *Chem. Int. Ed. Engl.* 33, 2009 (1994)) that concentration of sunlight gives rise to higher volume-to-time yields is erroneous. In contrast, at our geographical latitudes the volume-to-time yields are even higher when using a flat-bed solar light collector than by employing a parabolic trough concentrator. The essential use of flat-bed solar light collectors has so far been for detoxification, particularly for air and water, i.e. for the decomposition of low-molecular-weight compounds. We found that flat-bed solar light collectors are specially suited for the synthesis (building-up) of stereochemically and structurally complex compounds of higher molecularity.

For the purpose of satisfactory product yields, suntracking of a flat-bed solar light collector is not necessary establishing a low-tech/low-price technology.

Especially advantageous is a mirrored surface—advantageously as a surface-structured and radiation-reflecting metal or metal-coated plastic foil—at the inner site of the flat-bed solar light collector, e.g. at the bottom of the reactor (FIG. 1). In this way the solar radiation, which by penetrating the reaction media in direction of the bottom of the reactor is not absorbed and does therefore not lead to photochemical reactions, is further available by reflexion. In order to adjust the wavelength of the incident solar radiation to the individual demand of the reaction, the reactor can on the top be tightly (against solvents) covered with a transparent/UV-transparent glass or preferentially with a plastic foil. While carrying out photochemical reactions, proceeding sluggishly with UV light or light of other wavelengths, additional covering of the previously mentioned foil by an e.g. UV non-transparent layer can filter off the UV part or other wavelengths of the incident radiation.

BRIEF DESCRIPTION OF THE DRAWING

The invention will now be described in greater detail with reference to the drawing, wherein.

Figure 1:
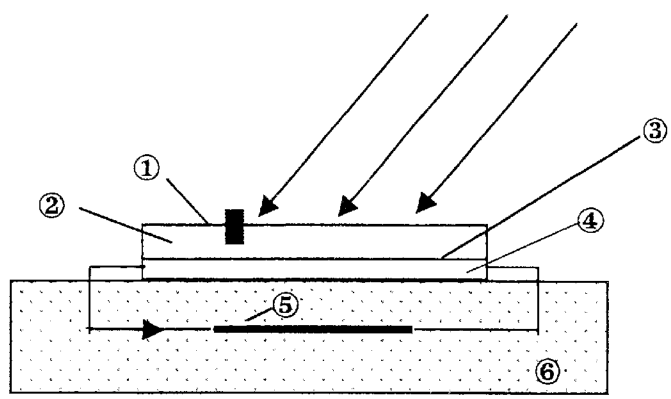
FIG. 1 is an illustration of a flat-bed solar light collector construct according to the present invention.

As a special construction, as shown in FIG. 1, the flat-bed solar light collector, equipped with a heat exchanger, can be used for the purpose of coupled or consecutive photonic and thermochemical processes. The heat exchanger is preferentially positioned below the reactor in a separate chamber charged with thermo-oil or an other thermal energy carrier (cooling chamber). From there the thermal transduction into the reaction chamber occurs via thermal conductivity. The thermal energy for the heating of the reactor is conveniently realized by a solar collector or a flat-bed solar light collector which delivers process heat energy via a temperature-steered pump to the heat exchanger.

For the purpose of carrying out photochemical reactions which need to be run at lower temperature, such as approximately +10° C., the collector can be coupled to a heat exchanger, preferentially positioned approx. 1 m in the ground (FIG. 1). Thus the collector becomes independent of cooling water or other cooling devices. In a special arrangement the flat-bed solar light collectors can be connected with each other by continuous flow tubings. In this way the synthesis product can be harvested from the last collector of the series. An appropriate detector (e.g. on the basis of light absorption), coupled to a pump, can serve for the steering of the flow of the reaction medium within the reactors. With the aid of a flat-bed solar light collector, electron transfer reactions can for example be performed for the synthesis of pharmaceutically relevant synthetic intermediates (examples 1–5) (for applications of such syntheses, see *Helv. Chim. Acta* 78, 2065 (1995) and *J. Am. Chem. Soc.* 119, 1129 (1997)). In particular, steroids and derivatives thereof can be synthesized with the aid of a flat-bed solar light collector in a very simple manner (see examples 6 and 7). Such compounds are being produced by e.g. Schering AG in large scale and are accepted generally as hormone regulating drugs (see example 6).

Furthermore, the flat-bed solar light collector is suitable for the photooxidation (photooxygenation) of terpene olefins and hence for the synthesis of industrially interesting flavours and fragrances such as rose oxide, myrtenol and myrtenal (perfumery industry; so far produced with conventional lamp technique, e.g. by Dragoco, Givaudan, Firmenich and Reimer & Haarnann). The flat-bed solar light collector can conveniently serve for the production of the fragrance rose oxide (see examples 8 and 9).

Furthermore, photochemical addition reactions (examples 1–7, 10 and 12) and rearrangements (examples 10 and 11) can be performed with the present flat-bed solar light collector (for further applications of this photochemistry, see Synthesis 1989, 145).

EXAMPLES

Comparison of a parabolic trough solar concentrator with a flat-bed solar light collector of the same apperture (example: solar photochemical synthesis of B via electron transfer):

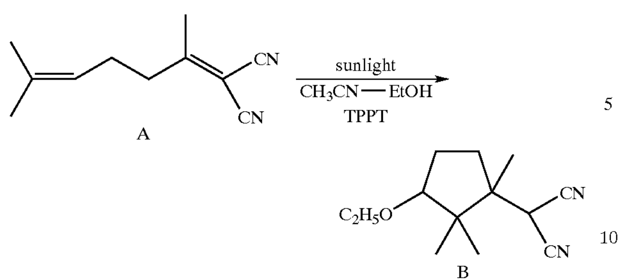

The given yields refer to amounts of isolated products. For the purpose of comparing the examples 1–3, every 30 min. a sample was taken to determine the turnover. The reactions were stopped at a turnover of approx. 50% and the reaction times were compared (see below). The turnover increases linearly with the time up to about 50%. The examples/experiments listed below were carried out in the solar plant on the roof of the MPI für Strahlenchemie in M ülheim an der Ruhr.

Example 1

Solution Used:

5,8 g≈33,33 mmol 2,6-dimethylhepta-1,5-diene-1,1-dicarbonitrile (A), 5,3g≈13,84 mmol 2,4,6 triphenylpyrylium-tetrafluoroborate (TPPT), 800 ml acetonitrile and 30 ml ethanol.

This solution was degassed with argon prior to reaction and kept under inert gas during irradiation.

600 ml of this solution was irradiated with sunlight in a parabolic trough solar concentrator for the duration of 8 hours. The weather was for the duration of 2 hours cloudy and for the residual time sunny (direct sunshine). Yield: 2.7 g; 51% B.

Example 2

230 ml of the solution, as defined in example 1, were irradiated with sunlight in a flat-bed solar light collector. After 4 hours the conversion was complete (weather: 2 hours sunny and 2 hours cloudy). Yield: 0,98 g; 48% B.

Example 3

230 ml of the solution as defined in example 1 were irradiated with sunlight in a flat-bed solar light collector for the duration of 6 hours on a cloudy day without any direct solar radiation. Yield: 1 g; 49% B.

For analytical data and structural assignment of A and B, see Ph.D. thesis in progress of K. D. Warzecha, MPI für Strahlenchemie/University of Essen.

Results: The reaction time to reach a yield of approx. 50% is shorter (4 hours in example 2 and 6 hours in example 3) by using a flat-bed solar light collector as compared to a parabolic trough solar concentrator which requires 8 hours of reaction time despite of 6 hours of direct sunshine.

Experiments using different solvent mixtures for the purpose of comparison are given below:

Example 4

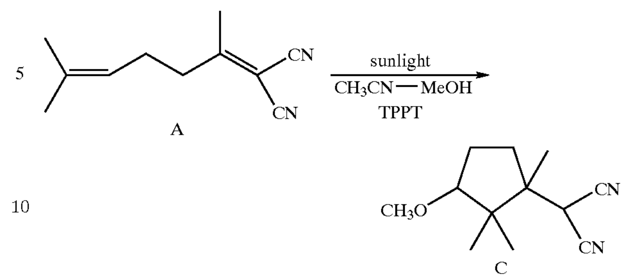

Solution Used:

3,4 g≈19 mmol 2,6-Dimethylhepta-1,5iene-1,1-dicarbonitrile (B) 5 g≈12,62 mmol 2,4,6 triphenylpyrylium-tetrafluoroborate (TPPT) 1275 ml acetonftrile and 125 ml methanol 700 ml of this solution were irradiated with sunlight in a flat-bed solar light collector for 3 hours:

The weather was during the first hour partly sunny/cloudy and during the second and third hour cloudy/partly rainy. Yield approx. 1,35 g; 63% (C)

Example 5

Parallel to example 4, 700 ml of the solution mentioned in this latter example were irradiated with sunlight in a parabolic trough concentrator under identical light and weather conditions: Less than 10% product yield.

Conclusion: Examples 4 and 5 demonstrate that on predominantly cloudy days the flat-bed solar light collector is considerably superior to the parabolic trough solar collector.

For analytical data and structural assignment of A and C, see Ph.D. thesis in progress of K. D. Warzecha, MPI für Strahlenchemie/University of Essen.

Examples of application:

Example 6

Steroid Synthesis (Complex Molecular Skeleton)

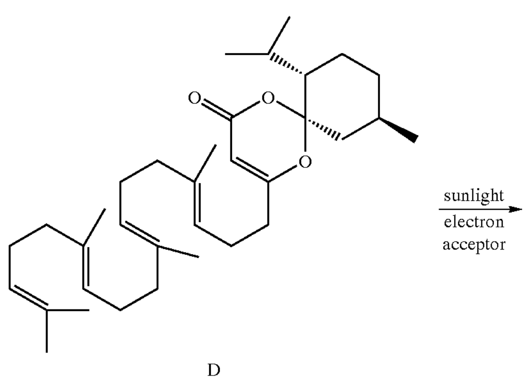

-continued

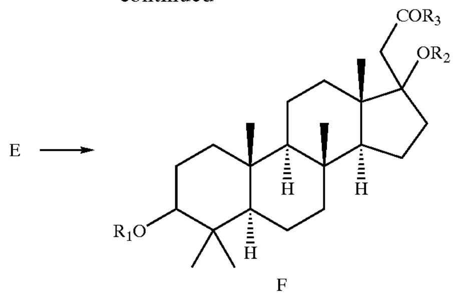

D (1,9 g), biphenyl (0,45 g) and 1,4-dicyano-2,3,5,6-tetramethylbenzene (0,22 g) were dissolved in acetonitrile/water (10:1) (330 ml) and the solution was degassed with a stream of argon for 15–20 min. before irradiation with sunlight in a flat-bed solar light collector for 3 days (weather: approx. 50% cloudy and 50% direct sunshine), until no D was any more detectable by thin layer chhromatography (tlc). The solution was then evaporated to dryness in a rotatory evaporator and the residual solid, a colourless/yellowish product mixture, was separated by column chromatography (silica gel; eluent: n-pentane/diethylether/diethylacetate 5:1:0 to 30:15:1). Yield of E: 15–25%).

E (1 g) was dissolved in abs. methanol (40 mL) before sodium methanolate in abs. methanol (25 ml, 0,5 molar) was added at 10° C. under argon; the reaction mixture was then stirred at room temperature before quenching with 80 ml of water and extraction with 300 ml of diethylether. Purification of the organic extract by column chromatography on silica gel (dichloromethane/diethylether 1:1) yielded 0,73 g F (95%).

For analogous examples with shorter chain polyalkene terpenoids, i.e. geranyl and farnesyl derivates, see M. Demuth, *Pure Appl. Chem.* 1999, in press.

For analytical data and structural assignment of D, E and F, see Ph.D. thesis in progress of K. D. Warzecha, MPI für Strahlenchemie/University of Essen.

Example 7

Steroid Synthesis (Complex Molecular Skeleton)

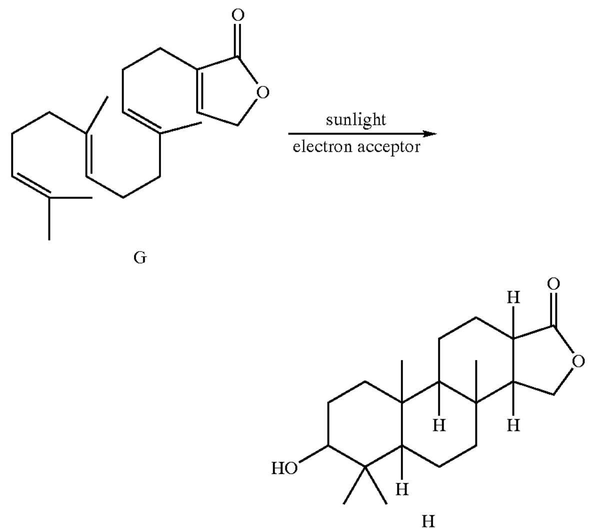

A solution of 220 ml acetonitrile/water (10:1), 0,5 g 3-farnesylmethyl-2(5H)-furanone (G), 0,094 g trimethyldicyanobenzene and 0,269 g biphenyl was irradiated with sunlight in a flat-bed solar light collector with an apperture of 0,1 $m^2$ for the duration of 5 days (weather: sunny, cloudy and partly rainy).

After evaporation of the solvent, the residue was purified chromatographically on silica gel 60 (0,04–0,063 mm, Merck, 100-fold) with pentane/ether 2:1. Yield: 0,0779 g 3-hydroxy-spongian-16-one (H) (15%).

For analytical data and structural assignment of G and H, see Ph.D. thesis in progress of F. Goeller, MPI für Strahlenchemie/University of Essen.

Example 8

Preparation of Rose Oxide (K) With Sunlight (Photooxygenation of Citronellol).

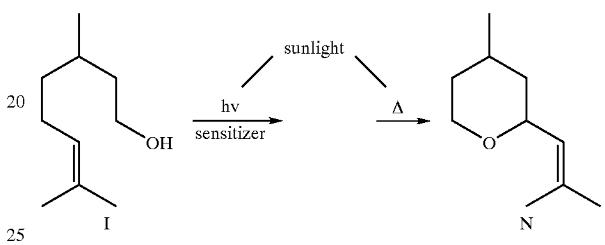

500 ml (429 g, 2.7 mol) citronellol (I)

400 ml methanol (J)

30 g rose bengal (K)

I, J and 6g of K were mixed and irradiated with sunlight in a flat-bed solar light collector by passing continuously air through the reaction solution. If the dark red solution turned brown during irradiation, again 6 g of K were added. Such additions were four times necessary during the three days of irradiation with sunlight (weather: approx. 50% cloudy and 50% direct sunshine).

The course of the reaction was monitored by thin layer chromatography.

After irradiation 800 ml conc. $Na_2SO_3$ solution (L) was added to the irradiated solution which was then heated in the flat-bed solar light collector to 70° C. for 3 hours (which can also be performed by direct solar radiation). After cooling of the solution to room temperature, the lower (aqueous) layer was removed and 500 ml of 5% sulfuric acid (M) were added to the remaining organic layer. After 30 min. water steam was passed through the solution and the distillate (mixture of oxides) was collected. 210 g of rose oxide (N) were collected after removal of the water.

For analytical data and structure assignments of I and N, see EP0842926 by Dragoco Gerberding & Co AG (1998).

Example 9

Application of Connected Flat-bed Solar Light Collectors in Series:

Production of rose oxide (N) with sunlight.

As in most of the previous examples, solar reactors of identical size (apperture 1 $m^2$) were employed in the following runs.

200 ml (172 g, 1.1 mol citronellol (I)

1 l methanol (J)

4 g rose bengal (K)

A mixture of I, J and K (3 g) was irradiated with sunlight in two flat-bed solar light collectors (each 0.5 $m^2$), connected in series, by passing air through the solution. The reaction solution was pumped through the reactors (approx. 2 l/hour) to enable continuous production. As soon as the dark red reaction medium turned brown during irradiation with sunlight, additional 1 g of K were added. The reaction time was 11 hours (weather: 70% cloudy and 30% direct sunshine).

After irradiation 300 ml conc. $Na_2SO_3$ solution (L) was added to the irradiated solution and which was then heated in the flat-bed solar light collector to 70° C. for 3 hours (which can be performed by direct solar radiation. After cooling of the solution to room temperature, the lower (aqueous) layer was removed and 200 ml of 5% sulfuric acid (M) were added to the organic layer. After 30 min., water steam was passed through the solution and the distillate (mixture of oxides) was collected. 88 g of rose oxide (N) were obtained after removal of the water.

For analytical data and structure assignments of I and N, see EP0842926 by Dragoco Gerberding & Co AG (1998).

Example 10

Preparation of a Stereochemically and Structurally Complex Product.

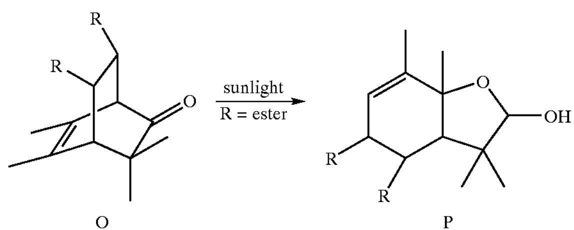

0,4 g of 3,3,5,6-tetramethyl-7,8-bismethoxycarbonylbicyclo[2.2.2]oct-5-en-2-one (O) were dissolved in 200 ml acetonitrile/water (9:1) and irradiated with sunlight in a flat-bed solar light collector (0,5 $m^2$ apperture) for 8 hours while passing a stream of argon through the reaction solution (weather: direct sunshine/cloudy/rainy). The solution was concentrated after irradiation and chromatographed/purified on silica gel 60 (0,04–0,063 mm, Merck, 100-fold) with pentane/acetone 10:1 as eluent. 0,37 g of 9-oxa-8-methoxy-1,2,7,7-tetramethyl-4,5-bismethoxycarbonylbicyclo-[4.3.0]non-2-ene (P) were obtained (48% yield). An identical experiment, but in a parabolic trough solar concentrator, took 3 days.

After irradiation 800 ml conc. $Na_2SO_3$ solution (L) was added to the irradiated solution which was then heated in the flat-bed solar light collector to 70° C. for 3 hours (which can be performed by direct solar radiation). After cooling of the solution to room temperature, the lower (aqueous) layer was removed and 500 ml of 5% sulfuric acid (M) were added to the remaining organic layer. After 30 min., water steam was passed through the solution and the distillate (mixture of oxides) was collected. 210 g of rose oxide (N) were obtained after removal of the water.

For analytical data and structural assignment of O and P, see Ph.D. thesis of A. Hülsdünker, MPI für Strahlenchemie/University of Essen (1994).

Example 11

Comparison of Flat-bed Solar Fight Collectors, Connected in Series, With a Parabolic Trough Solar Concentrator:

Photochemical rearrangement (oxa-di-pi-methane rearrangement).

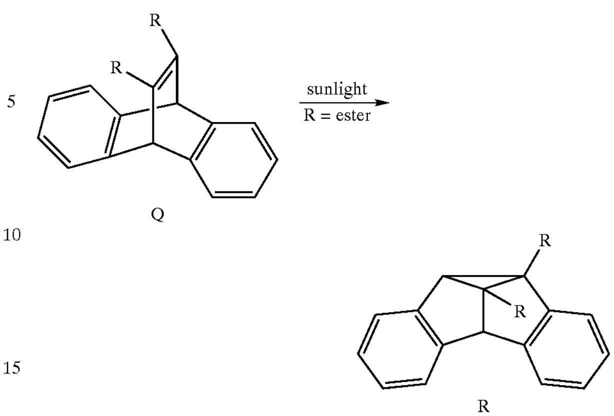

Two halves of a solution of acetonitrile (1,9 1), 11 g of 9,10-dihydro-9,10-(11,12-bismethoxycarbonyl)ethenoanthracene (Q) and 75 ml acetophenone were irradiated with sunlight each in parallel in a parabolic trough solar concentrator and a flat-bed solar light collectors connected in series.

Two flat-bed solar light collector were—as mentioned in example 9—connected in series (each of 0.5 $m^2$ apperture) through which the reaction solution was pumped continuously. Reaction time for both reactors: 90 min.

Work-up:

After concentration of the solution, the residue was chromatographed on silica gel 60 (Merck, 80-fold) using pentane/ether (90:10) as eluent. The reaction performed in the flat-bed solar light collector afforded 4,45 g of R (yield: 81%) and the one in the parabolic trough solar concentrator 0,9 g of R (yield: approx. 16%). For analytical data and structural assignment of 0 and P, see Ph.D. thesis of A. Hülsd ünker, MPI für Strahlenchemie/University of Essen (1994).

Example 12

Cycloaddition (Addition Reaction) as Intermediate Step for the Preparation of the Taxane ABC Rings (Precursor of a Complex Biological Agent).

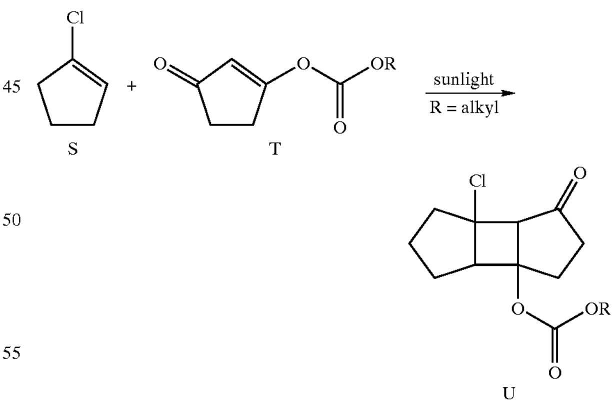

A solution of 18.5 g of T and 180 ml of S in toluene (360 ml) was irradiated in sunlight in a flat-bed solar light collector (0,5 $m^2$ apperture) for 10 hours under argon. After evaporation of the solvent, the residue was purified by column chromatography (silica gel 60, 0,04–0,063 mm) using pentane/ethylacetate (20:1 o 8:1) as eluent to yield U in 54% yield.

An identical experiment, but in a parabolic trough solar concentrator, took 4 days of reaction time.

For analytical data and structural assignment of S, T and U, see Ph.D. thesis of D. Sträubig, MPI für Strahlenchemie/University of Essen (1997).

What is claimed is:

1. A process for producing a desired product, said process comprising the following steps:

a) providing at least one flat-bed solar light collector comprising at least one reaction chamber;

b) introducing one or more reactants to the at least one reaction chamber, said one or more reactants being unsupported, and said one or more reactants being different in said desired product;

c) irradiating the reaction chamber with direct or diffused sun light or direct or indirect artificial light without a device for focusing the light, said irradiating causing the one or more reactants to undergo a reaction to produce said desired product or a precursor of said desired product; and d) in case step c) yields said desired product, purifying said desired product; or e) in case step c) yields a precursor of said desired product, converting said precursor to said desired product.

2. The process according to claim 1, wherein an inner surface of the flat-bed solar light collector is light reflecting.

3. The process according to claim 1, wherein the solar light collector is equipped with at least one transparent, wavelength-selective cover.

4. The process according to claim 3, wherein the wavelength-selective cover is a fluorinated polymer foil.

5. The process according to claim 1, wherein the flat-bed solar light collector is coupled to a beat exchanger.

6. The process according to claim 5, wherein the heat exchanger is coupled to a process heat delivering solar collector or a flat-bed solar light collector.

7. The process according to claim 6, wherein the heat exchanger is additionally connected to an underground heat exchanger.

8. The process according to any one of claims 1–7, wherein the desired product is selected from the group consisting of flavors, fragrants and aromas.

9. The process according to claim 8, wherein the desired product is selected from the group consisting of flavors and fragrants, and the reaction is a photooxygenation reaction.

10. The process according to claim 9, wherein the desired product is selected from the group consisting of rose oxide myrtenol and myrtenal.

11. The process according to any one of claims 1–7, wherein the desired product is selected from the group consisting of steroids, and the reaction is an electron transfer reaction.

12. The process according to any one of claims 1—7, wherein the desired product is selected from the group consisting of complex biologically active agents and precursors thereof, and the reaction is selected from the group consisting of rearrangement and addition reactions.

13. The process according to claim 1, wherein a plurality of flat-bed solar light collectors are connected in series and are operated at continuous flow.

14. The process according to claim 13, wherein the desired product or precursor thereof is continuously collected and removed from a flat-bed solar light collector positioned last in the series by means of a pumping system, and a corresponding amount of said one or more reactants is recharged into a flat-bed solar light collector positioned first in the series.

* * * * *

UNITED STATES PATENT AND TRADEMARK OFFICE

CERTIFICATE OF CORRECTION

PATENT NO. : 6,660,132 B1
DATED : December 9, 2003
INVENTOR(S) : Demuth et al.

It is certified that error appears in the above-identified patent and that said Letters Patent is hereby corrected as shown below:

Column 10,
Lines 11-12, "rose oxide myrtenol" should read -- rose oxide, myrtenol --

Signed and Sealed this

Eighth Day of March, 2005

JON W. DUDAS
*Director of the United States Patent and Trademark Office*